United States Patent [19]

Patel

[11] 4,175,567

[45] Nov. 27, 1979

[54] METHOD OF LOCATING THE EPIDURAL SPACE

[75] Inventor: Bhupendra C. Patel, Elgin, Ill.

[73] Assignee: The Kendall Company, Boston, Mass.

[21] Appl. No.: 889,477

[22] Filed: Mar. 23, 1978

Related U.S. Application Data

[62] Division of Ser. No. 680,955, Apr. 28, 1976, abandoned.

[51] Int. Cl.$^2$ .............................................. A61B 5/00
[52] U.S. Cl. ..................................... 128/748; 128/774
[58] Field of Search ............... 128/2 B, 2 R, 2.05 D, 128/2.05 E; 73/700, 715, 730; 116/70, 114 C, 114 AJ, 114 PV, 117 C, 118 R

[56] References Cited

U.S. PATENT DOCUMENTS

| 3,625,199 | 12/1971 | Summers | 128/2.05 D |
| 3,675,722 | 7/1972 | Balmes, Sr. | 116/114 PV |
| 3,736,899 | 6/1973 | Manske | 116/114 PV |
| 3,874,369 | 4/1975 | Pannier, Jr. et al. | 128/2.05 D |

*Primary Examiner*—William E. Kamm
*Attorney, Agent, or Firm*—Powell L. Sprunger

[57] ABSTRACT

A method of locating the epidural space in a patient's body with a needle assembly having a flexible film defining a closed cavity which communicates with a needle of the assembly, comprising the steps of positioning a tip of the assembly adjacent the epidural space, and advancing the assembly into the body while determining whether the film flexes inwardly or outwardly relative to the assembly to ascertain the position of the needle assembly tip in the patient's body.

6 Claims, 12 Drawing Figures

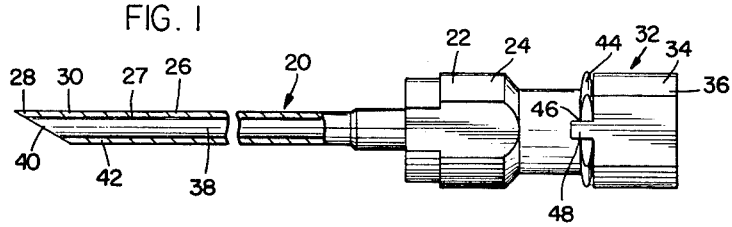
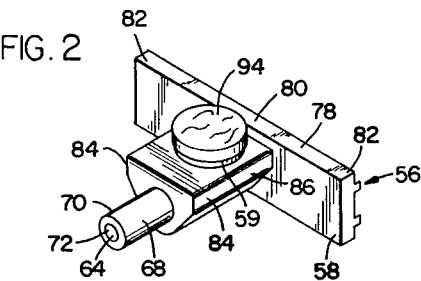
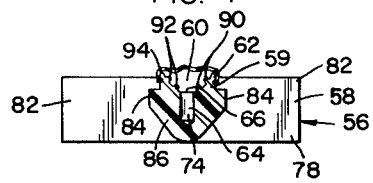
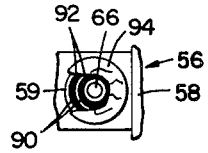
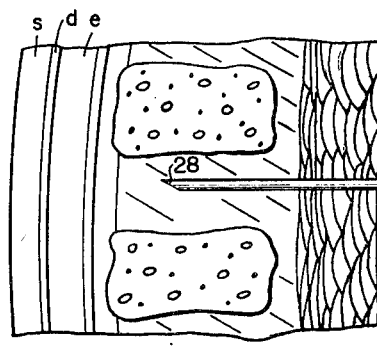

METHOD OF LOCATING THE EPIDURAL SPACE

This is a division of application Ser. No. 680,955 filed Apr. 28, 1976, now abandoned.

BACKGROUND OF THE INVENTION

The present invention relates to position testing devices for a patient's body.

During certain medical procedures, such as an epidural anesthesia procedure, it is necessary to position the tip of a needle at a relatively precise position inside the patient's body. During this particular procedure, the needle tip should be located in the potential epidural space where the body pressure is normally slightly negative, and never positive. If the needle tip has been advanced too far into the body, it projects through the dura mater into the subarachnoid space where the body pressure is positive.

Epidural anesthesia has become popular among anesthesiologists and surgeons since it does not entail the risks associated with general anesthesia, and does not require that the dura mater be punctured. However, locating the epidural space can be relatively difficult since it is a potential space, i.e., an interface between two tissues which are normally held together by a slight negative pressure. Prior testing methods for the epidural space involve the use of tactile sense with syringes or a drop of liquid placed on the needle hub. The syringe tests have not been satisfactory since they rely on subjective judgment of the user under his control. The hub or Guiteras test also has not been suitable since the liquid drop frequently falls out of the hub, and thus may result in a false indication of the needle location.

SUMMARY OF THE INVENTION

A principal feature of the present invention is the provision of a method for locating the epidural space in a patient's body with a needle assembly.

The needle assembly used in the applicant's method has a distal tip, a proximal indicating surface or raised member, with an overlying flexible film, and a passageway communicating between the tip and a closed space beneath the film. When the film flexes against the indicating surface or raised member, the visibility of the indicating surface is modified through the film or the raised member impresses a pattern on the film, respectively.

A feature of the invention is that the user may ascertain the position of the assembly tip relative to the epidural space by determining whether the film flexes toward or away from the indicating surface or raised member as the assembly is advanced into the body.

Another feature of the invention is that the advancement of the assembly is stopped if the film flexes toward the indicating surface or raised member since the tip is located in the epidural space.

Yet another feature of the invention is that the assembly is withdrawn and the procedure is partially repeated if the film flexes outwardly from the indicating surface or raised member since the tip has passed through the dura mater into the subarachnoid space.

Further features will become more fully apparent in the following description of the embodiments of this invention and from the appended claims.

DESCRIPTION OF THE DRAWINGS

In the drawings:

FIG. 1 is a fragmentary elevational view, taken partly in section, of a spinal needle and stylet;

FIG. 2 is a perspective view of a position testing device of the present invention;

FIG. 3 is a top plan view of the testing device of FIG. 2;

FIG. 4 is a sectional view taken substantially as indicated along the line 4—4 of FIG. 3;

FIG. 5 is a sectional view taken substantially as indicated along the line 5—5 of FIG. 3;

FIG. 6 is a fragmentary plan view showing a film of the device prior to contact with an indicating surface;

FIG. 7 is a fragmentary plan view, partly broken away, showing an embodiment of an indicating surface for the device of FIG. 2;

FIG. 8 is a diagrammatic sectional view of a patient's body showing the needle and stylet of FIG. 1 as positioned in the patient;

DESCRIPTION OF THE PREFERRED EMBODIMENTS

Figure 9:
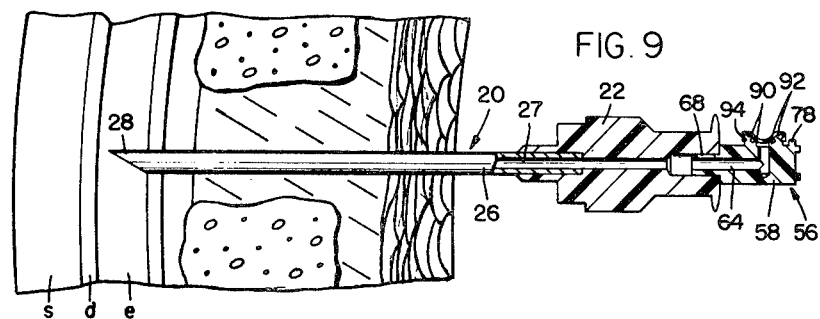
FIG. 9 is a diagrammatic sectional view of the patient's body showing the needle tip as positioned in the epidural space of the patient.

Referring now to FIG. 1, there is shown a hollow spinal needle generally designated 20 having a hub 22 adjacent a proximal end 24 of the needle, a hollow shaft 26 secured to the hub 22, a lumen 27, and a bevel tip 28 adjacent a distal end 30 of the needle 20. As shown, a stylet generally designated 32 is removably received in the needle 20. The stylet 32 has an end member 34 adjacent a proximal end 36 of the stylet 32, a solid shaft 38 connected to the member 34 and received in the hollow shaft 26 of the needle 20, with the shaft 38 having a bevel tip 40 adjacent a distal end 42 of the stylet 32 forming a continuous distal end surface between the needle tip 28 and stylet tip 40 when the stylet 32 is properly positioned within the needle 20. The needle hub 22 has an outwardly directed flange 44 at its proximal end, and the flange 44 has a reference notch 46 to receive a reference protuberance 48 extending distally of the stylet member 34. Accordingly, the stylet 32 may be rotated within the needle 20 until the protuberance 48 is located in the notch 46, as shown, such that the flange 44 and member 34 mate together and position the stylet tip 40 at its proper location relative the needle tip 28.

With reference to FIG. 8, at the start of an epidural anesthesia procedure, a patient may be positioned on his side and the needle 20 and internal stylet 32 are inserted by the physician into the patient's back until needle and stylet tips are located somewhat near the epidural space e of the patient. During this time, the stylet 32 prevents coring of body tissue by the needle 20. After the needle 20 has been properly positioned in the patient, the stylet 32 is removed from the needle, as will be described below.

With referene to FIGS. 2-5, there is shown a testing device generally designated 56 having a body member 58. The body member 58 has an annular extension 59 defining a cavity 60 at an outer surface 62 of the extension 59. The body member 58 has a passageway 64 communicating with a lower end of the cavity 60 at an opening 66. The body member 58 also has a tubular section 68 at a distal end 70 of the body member 58, with the tubular section 68 defining an outer end portion of the passageway 64 and an opening 72 at the distal end of the body member. As shown, the passageway 64 has a first channel 74 communicating with the cavity opening 66 and disposed generally vertically when the cavity 60 is placed in an upright position, and a second channel 76 disposed generally horizontally during testing and communicating between the channel 74 and the end opening 72. The body member 58 also has an elongated bar 78 at a proximal end 80 of the body member 58 defining a pair of opposed wings 82 which extend past opposed sides 84 of the body member 58. As shown, a central portion 86 of the body member 58 connects the tubular section 68 and the elongated bar 78. The body member 58 may be made of any suitable material, such as plastic.

With reference to FIGS. 4, 5, and 7, the body member 58 has a plurality of raised members 90 defining relatively flat indicating surfaces 92 which are recessed in the cavity 60. In the embodiment shown, the raised members 90 comprise a pair of concentric rings, with the opening 66 communicating with the cavity inside the smaller inner ring. With reference to FIG. 7, the indicating surfaces 92 may have a color contrast, such as red or black, for a purpose which will be described below.

Figure 11:
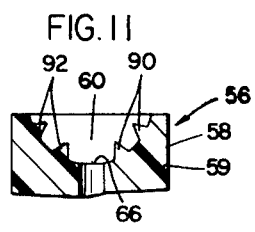
FIG. 11 is a fragmentary sectional view of another embodiment of the device of the present invention.

With reference to FIGS. 2-7, the device 56 also has a flexible film 94 secured to the extension 59 over the raised members 90 and closing the cavity 60. As shown in FIGS. 4 and 5, the indicating surfaces 92 face the film 94, and the film 94 is normally spaced from the surfaces 92. In one embodiment, the film 94 may be made of a transparent or translucent material, such as polyethylene, and in another embodiment may be made of an opaque material, such as rubber. If the film 94 is translucent or transparent, the indicating surfaces 92 of the raised members 90 are barely visible, if at all, when the film 94 is spaced from the surfaces 92, as shown in FIG. 6. However, when the film 94 contacts the indicating surfaces 92, the surfaces 92 become readily visible through the film 94. Visibility of the surfaces 92 through the film 94 is enhanced by the color contrast on the surfaces 92, as previously described in connection with FIG. 7. Alternatively, if the film 94 is opaque, the pattern of the raised members 90 is impressed on the film when the film 94 is drawn against the raised members 90. In this case, with reference to FIG. 11, impression of the pattern by the raised members 90 is enhanced by the tapered members 90 defining lines for the indicating surfaces 92 facing the film.

Figure 10:
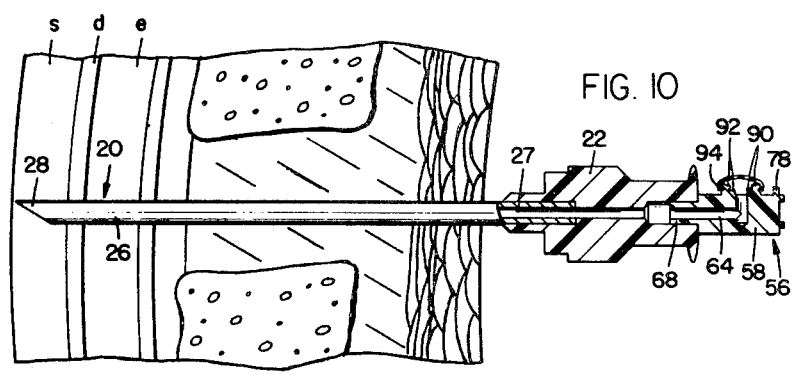
FIG. 10 is a diagrammatic sectional view of the patient's body showing the needle tip as positioned in the subarachnoid space of the patient.

The use of the device 56 for testing the needle location in a patient's body is described as follows. With reference to FIGS. 8-10, after the needle 20 and stylet 32 have been positioned in the body, as previously described, the stylet 32 is removed from the needle 20. Next, the testing device is attached to the needle hub 22 by positioning the tubular section 68 of the body member 58 in the lumen 27 of the hub 22, and with the film 94 the device 56 located in an upright position to permit clear vision of the film. Referring to FIG. 9, the physician grasps the opposed wings of the bar 78, and advances the needle 20 and the attached body member 58 slightly into the patient's body. When the needle tip is located in the epidural space e of the patient, the needle tip communicates with a slight negative pressure in the epidural space e, causing the film 94 to be drawn against the indicating surfaces 92 of the raised members 90. In the case of a translucent or transparent film, the indicating surfaces 92 will become readily visible through the film 94, while in the case of an opaque film, a pattern will be impressed on the film 94 by the raised members 90. In both cases, visibility of the indicating surfaces or the impressed pattern indicates that the needle tip 28 is properly located in the epidural space e of the patient. However, with reference to FIG. 10, if the needle tip 28 has been inadvertently passed through the dura mater d into the subarachnoid space s, the needle tip 28 communicates with a positive pressure in the subarachnoid space s causing the film 94 to flex outwardly from the body member. Accordingly, the inflated film 94 also indicates whether the needle tip has improperly punctured the dura mater d, in which case the needle 20 must be withdrawn a slight distance from the patient, and the device may be again used to determine when the needle tip 28 has been located in the epidural space e. After the needle has been properly positioned in the patient with the needle tip 28 located in the epidural space e, the testing device 56 is removed from the needle hub 22, and the epidural anesthesia procedure proceeds in the normal manner.

Thus, in accordance with the present invention the testing device permits easy attachment and removal of the body member 58 from the needle hub 22, and provides a sure indication when the needle tip has been properly positioned in the epidural space e of the patient. The testing device 56 also indicates whether the needle tip 28 has been improperly positioned in the subarachnoid space s of the patient. Alternatively, during certain procedures it is necessary to position the needle tip in the subarachnoid space, and the device of the present invention may be used to indicate when the needle tip has punctured the dura mater and is properly located in the body.

Figure 12:
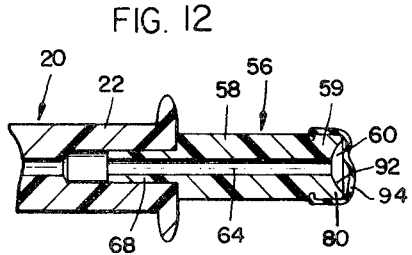
FIG. 12 is a sectional view of another embodiment of the testing device of the present invention.

Another embodiment of the present invention is illustrated in FIG. 12, in which like reference numerals designate like parts. In this embodiment, the annular extension 59 defining the cavity 60 is located at the proximal end 80 of the body member 58. The film 94 is secured over the cavity 60 in a manner as previously described. However, in this embodiment, the body member 58 defines a continuous indicating surface 92 which underlies the film 94, and the film 94 is preferably translucent or transparent to indicate when the film 94 contacts the indicating surface 92 responsive to a negative pressure in the passageway 64.

According to a method of the present invention the position of a needle assembly in a patient's body is tested by advancing a tip of the assembly into the patient's body, and modifying the visibility of an indicating surface through a film responsive to a change of body pressure adjacent the tip. According to another method of the invention, the position of the assembly is tested by advancing a tip of the assembly into a patient's body, and by impressing a pattern on a film responsive to a negative pressure in the assembly.

The foregoing detailed description is given for clearness of understanding only, and no unnecessary limitations should be understood therefrom, as modificatons will be obvious to those skilled in the art.

I claim:

1. A method of locating the epidural space in a patient's body with a needle assembly having a distal tip, a proximal indicating surface, a flexible film overlying the indicating surface and permitting vision of said surface through the film when the film flexes toward the indicating surface, and a passageway communicating between the tip and a closed space intermediate the indicating surface and film, comprising the steps of:

positioning the tip and a distal passageway portion of the assembly inside the patient's body with the tip located adjacent the epidural space and with the film and indicating surface located outside the patient's body; and advancing the assembly into the body while determining whether the visibility of the indicating surface is modified through the film or the film flexes away from the indicating surface to ascertain the position of the needle assembly tip in the patient's body.

2. The method of claim 1 including the step of withdrawing the assembly slightly from the patient's body and repeating the advancing step if the film flexes away from the indicating surface.

3. The method of claim 1 including the step of stopping advancement of the assembly if the visibility of the indicating surface through the film is modified.

4. A method of locating the epidural space in a patient's body with a needle assembly having a distal tip, a proximal raised member, a flexible film overlying the raised member such that the raised member impresses a pattern on the film when the film flexes against the raised member, and a passageway communicating between the tip and a closed space intermediate the film and raised member, comprising the steps of:

positioning the tip and a distal passageway portion of the assembly inside the patient's body with the tip located adjacent the epidural space and with the film and raised member located outside the patient's body; and advancing the assembly into the body while determining whether the raised member impresses a pattern on the film or the film flexes away from the raised member to ascertain the position of the needle assembly tip in the patient's body.

5. The method of claim 4 including the step of withdrawing the assembly slightly from the patient's body and repeating the advancing step if the film flexes away from the raised member.

6. The method of claim 4 including the step of stopping advancement of the assembly if the raised member impresses a pattern on the film.

* * * * *